US012796993B2

(12) United States Patent
Li et al.

(10) Patent No.: US 12,796,993 B2
(45) Date of Patent: Nov. 17, 2026

(54) METHOD FOR SAMPLING BIOMETRIC DATA AND SAMPLING AND MANAGING APPARATUS THEREOF

(71) Applicant: SHENZHEN GOODIX TECHNOLOGY CO., LTD., Shenzhen (CN)

(72) Inventors: Shibai Li, Shenzhen (CN); Peng Wan, Shenzhen (CN); Hailin Yin, Shenzhen (CN); Saiwen Lu, Shenzhen (CN)

(73) Assignee: SHENZHEN GOODIX TECHNOLOGY CO., LTD. (CN)

(*) Notice: Subject to any disclaimer, the term of this patent is extended or adjusted under 35 U.S.C. 154(b) by 1328 days.

(21) Appl. No.: 17/134,109

(22) Filed: Dec. 24, 2020

(65) Prior Publication Data

US 2021/0161454 A1 Jun. 3, 2021

Related U.S. Application Data

(63) Continuation of application No. PCT/CN2019/121982, filed on Nov. 29, 2019.

(51) Int. Cl.

| | |
|---|---|
| ***A61B 5/308*** | (2021.01) |
| ***A61B 5/00*** | (2006.01) |
| ***A61B 5/024*** | (2006.01) |
| ***G16H 10/00*** | (2018.01) |
| ***G16H 10/60*** | (2018.01) |

(52) U.S. Cl.

CPC ................ *A61B 5/308* (2021.01); *A61B 5/72* (2013.01); *A61B 5/02416* (2013.01); *G16H 10/00* (2018.01); *G16H 10/60* (2018.01)

(58) Field of Classification Search

CPC ....... A61B 5/308; A61B 5/72; A61B 5/02416; G16H 10/60; G16H 10/00

See application file for complete search history.

(56) References Cited

U.S. PATENT DOCUMENTS

| | | | | |
|---|---|---|---|---|
| 6,363,269 | B1 * | 3/2002 | Hanna ................ | A61B 5/14551 600/336 |
| 7,062,307 | B2 * | 6/2006 | Norris ................ | A61B 5/14551 600/336 |
| 2003/0204140 | A1 | 10/2003 | Ferek-Patric et al. | |
| 2007/0257825 | A1 | 11/2007 | Woodward et al. | |
| 2010/0240980 | A1 | 9/2010 | Zhu et al. | |
| 2011/0066010 | A1 * | 3/2011 | Moon ................. | A61B 5/0205 600/509 |
| 2011/0201946 | A1 | 8/2011 | Turcott | |
| 2012/0257698 | A1 | 10/2012 | Zhang | |
| 2014/0171749 | A1 | 6/2014 | Chin et al. | |
| 2014/0223114 | A1 | 8/2014 | Wang et al. | |
| 2017/0134216 | A1 * | 5/2017 | Bitar ..................... | H04L 41/085 |
| 2019/0269334 | A1 | 9/2019 | Addison et al. | |

FOREIGN PATENT DOCUMENTS

| | | | | |
|---|---|---|---|---|
| CN | 1749985 | A | 3/2006 | |
| CN | 101436046 | A | 5/2009 | |
| CN | 201782756 | U | 4/2011 | |
| CN | 202025320 | U | 11/2011 | |
| CN | 104656514 | A | 5/2015 | |
| CN | 106874083 | A | 6/2017 | |
| CN | 107710625 | A | 2/2018 | |
| CN | 108198527 | A | 6/2018 | |
| CN | 109065145 | A | 12/2018 | |
| CN | 109077722 | A | 12/2018 | |
| CN | 110470803 | A | 11/2019 | |
| KR | 1020180109693 | A | 10/2018 | |
| KR | 1020190087538 | A | 7/2019 | |
| KR | 1020190118190 | A | 10/2019 | |
| WO | WO2015096433 | A1 | 7/2015 | |
| WO | WO-2019101222 | A2 * | 5/2019 | ........ H04W 52/0277 |

OTHER PUBLICATIONS

Tamura. "Current progress of photoplethysmography and SPO2 for health monitoring." Biomedical Engineering Letters, (Published online: Feb. 18), vol. 9, pp. 21-36. (Year: 2019).*

Warren et al. "Improving Pulse Rate Measurements during Random Motion Using a Wearable Multichannel Reflectance Photoplethysmograph." Sensors, vol. 16, No. 342, pp. 1-18. (Year: 2016).*

Budidha et al. "Design and Development of a Modular, Multichannel Photoplethysmography System." IEEE Transactions on Instrumentation and Measurement, vol. 67, No. 8, pp. 1954-1965. (Year: 2018).*

Chua et al. "Mixed Bio-Signal Lossless Data Compressor for Portable Brain-Heart Monitoring Systems." IEEE Transactions on Consumer Electronics, vol. 57, No. 1, pp. 267-273. (Year: 2011).*

Ozkan et al. "A Portable Wearable Tele-ECG Monitoring System." IEEE Transactions on Instrumentation and Measurement, (First published Mar. 20, 2019), vol. 69, Issue 1, pp. 173-182. (Year: 2020).*

(Continued)

*Primary Examiner* — Joseph Woitach
*Assistant Examiner* — Steven W. Bailey
(74) *Attorney, Agent, or Firm* — Emerson, Thomson & Bennett, LLC; Roger D. Emerson; Peter R. Detorre

(57) ABSTRACT

A method for sampling biometric data, a sampling and managing apparatus thereof, an apparatus for detecting biometric data, and an electronic device are provided. The method for sampling biometric data includes: determining, based on a preset sampling rule, a sampling configuration corresponding to a sampling time slot in a sampling refresh period, the sampling refresh period including a plurality of the sampling time slots; and controlling, based on the sampling configuration corresponding to the sampling time slot in the sampling refresh period, a sampling channel corresponding to the sampling time slot to sample a target signal to obtain sample data associated with the biometric data, thereby improving the flexibility in sampling process control.

8 Claims, 4 Drawing Sheets

(56) References Cited

OTHER PUBLICATIONS

Li An-yang, Yang Wen-sheng, He Min, Hardware design of mufti-channel and signals high-precision detection system based on FPGA and DSP, Journal of Mechanical & Electrical Engineering, Oct. 20, 2016, vol. 33 No. 10.
Liu Hai, FPGA-based Multi-Channel Data Acquisition Terminal Design, The Fourtune Times, Oct. 15, 2018, Issue No. 10.
Chen,Shih-Lun, “A Power-Efficient Adaptive Fuzzy Resolution Control System for Wireless Body Sensor Networks”, IEEE Access, vol. 3, Jun. 1, 2015, pp. 743-751.

* cited by examiner

METHOD FOR SAMPLING BIOMETRIC DATA AND SAMPLING AND MANAGING APPARATUS THEREOF

CROSS-REFERENCE TO RELATED APPLICATION

The present disclosure is a continuation of international application No. PCT/CN2019/121982 filed on Nov. 29, 2019, and entitled "METHOD FOR SAMPLING BIOMETRIC DATA AND SAMPLING AND MANAGING APPARATUS THEREOF", which is hereby incorporated by reference in its entirety.

TECHNICAL FIELD

Embodiments of the present disclosure relate to the field of data processing technologies, and in particular to, a method for sampling biometric data, a sampling and managing apparatus thereof, an apparatus for detecting biometric data, and an electronic device.

BACKGROUND

Sampling of biometric data is widely used in various application scenarios. For example, in an application scenario of biometric detection, biometrics of a human body are detected to provide a user with some health or exercise suggestions, specifically, e.g., heart rate of the biometrics. Taking heart rate detection as an example, an existing technology provides a multi-channel heart rate detection solution, which specifically includes sampling processing and heart rate computation, where the sampling processing is implemented mainly based on multi-channel sampling. However, the sampling processing provided in the existing technology has poor flexibility in sampling process control.

SUMMARY

In view of this, one of the technical problems to be solved by embodiments of the present disclosure is to provide a method for sampling biometric data, a sampling and managing apparatus thereof, an apparatus for detecting biometric data, and an electronic device, to overcome or relieve the above defects in existing technologies.

An embodiment of the present disclosure provides a method for sampling biometric data, including:

determining, based on a preset sampling rule, a sampling configuration corresponding to a sampling time slot in a sampling refresh period, the sampling refresh period including a plurality of the sampling time slots; and controlling, based on the sampling configuration corresponding to the sampling time slot in the sampling refresh period, a sampling channel corresponding to the sampling time slot to sample a target signal to obtain sample data associated with the biometric data.

An embodiment of the present disclosure further provides a sampling and managing apparatus for biometric data, including:

a determining unit configured to determine, based on a preset sampling rule, a sampling configuration corresponding to a sampling time slot in a sampling refresh period, the sampling refresh period including a plurality of the sampling time slots; and a controlling unit configured to control, based on the sampling configuration corresponding to the sampling time slot in the sampling refresh period, a sampling channel corresponding to the sampling time slot to sample a target signal to obtain sample data associated with the biometric data.

An embodiment of the present disclosure further provides an apparatus for detecting biometric data, including the sampling and managing apparatus for biometric data according to any one embodiment of the present disclosure.

An embodiment of the present disclosure further provides an electronic device, including: a master controller and the sampling and managing apparatus for biometric data according to any one embodiment of the present disclosure, the master controller controlling the sampling and managing apparatus to sample a target signal to obtain sample data associated with the biometric data.

In the technical solutions of the embodiments of the present disclosure, when biometric data is sampled, a sampling configuration corresponding to a sampling time slot in a sampling refresh period is determined based on a preset sampling rule, the sampling refresh period including a plurality of the sampling time slots; and a sampling channel corresponding to the sampling time slot is controlled based on the sampling configuration corresponding to the sampling time slot in the sampling refresh period, to sample a target signal to obtain sample data associated with the biometric data, thereby improving the flexibility in sampling process control.

BRIEF DESCRIPTION OF THE DRAWINGS

Some specific embodiments of embodiments of the present disclosure will be described in detail below with reference to the accompanying drawings in an example manner, instead of a limiting manner. Identical reference numerals in the accompanying drawings represent identical or similar components or parts. It should be understood by those skilled in the art that these accompanying drawings may not be drawn to scale. In the drawings.

DETAILED DESCRIPTION

Any technical solution in embodiments of the present disclosure may not necessarily be implemented to achieve all of the above advantages.

To enable those skilled in the art to better understand the technical solutions in the embodiments of the present disclosure, the technical solutions in the embodiments of the present disclosure will be clearly and completely described below with reference to the accompanying drawings in the embodiments of the present disclosure. Apparently, the described embodiments are merely a part, instead of all, of the embodiments of the present disclosure. All other embodiments obtained by those of ordinary skills in the art based on the embodiments of the present disclosure should fall within the scope of protection of the embodiments of the present disclosure.

Specific implementations of the embodiments of the present disclosure will be further described below with reference to the accompanying drawings of the embodiments of the present disclosure.

Figure 1:
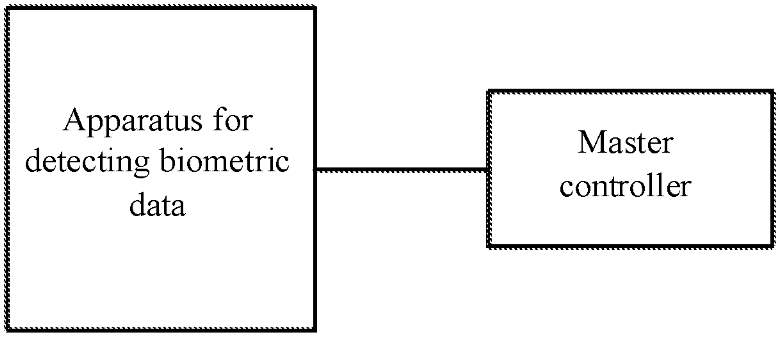
FIG. 1 is a schematic diagram of an electronic device applying a technical solution for sampling biometric data in Embodiment I of the present disclosure.

FIG. 1 is a schematic diagram of an electronic device with a technical solution for sampling biometric data in Embodiment I of the present disclosure. As shown in FIG. 1, the electronic device includes an apparatus for detecting biometric data and a master controller, and the master controller is configured to control the apparatus for detecting biometric data to sample a target signal to obtain sample data associated with the biometric data. The apparatus for detecting biometric data may specifically include a sampling and managing apparatus and a sampling channel. The sampling and managing apparatus is configured to execute a sampling and managing method in an embodiment shown in FIG. 2 below, to sample the target signal through the sampling channel.

The electronic device in the embodiments of the present disclosure exists in various forms, including but not limited to:

(1) an electronic apparatus having data interaction functions, e.g., a smart bracelet, or a smart earphone.

(2) a mobile communication device: Such a device is characterized by having mobile communication functions, and is mainly intended to provide voice and data communication. Such a terminal includes: a smart phone (e.g., an iPhone), a multimedia phone, a functional phone, a low-end phone, and the like.

(3) an ultra-mobile personal computer device: Such a device belongs to a category of personal computers, has computing and processing functions, and generally also has the characteristics of mobile Internet access. Such a terminal includes: a device, such as a PDA, a MID, and a UMPC, e.g., an iPad.

(4) a portable entertainment device: Such a device can display and play multimedia contents. Such a device includes: an audio player, a video player (e.g., an iPod), a handheld game player, an e-book, and a smart toy.

(5) a server: A device providing a computing service. The server components include a processor, a hard disk, an internal memory, a system bus, etc. A structure of the server is similar to that of a general computer. But because of the needs of providing a highly reliable service, the requirements in respect of processing capacity, stability, reliability, security, scalability, manageability, etc. are very high.

When some specific application modes, e.g., biometric detection, are implemented through the electronic device, the master controller may be further configured to perform biometric detection based on the sample data. The biometrics are at least one of blood oxygen saturation, pulse rate, heart rate, respiratory rate, respiratory volume, blood pressure, or hemoglobin.

A detailed process of controlling the sampling channel by the sampling and managing apparatus for biometric data to sample the target signal will be explained below by way of an example.

Figure 2:
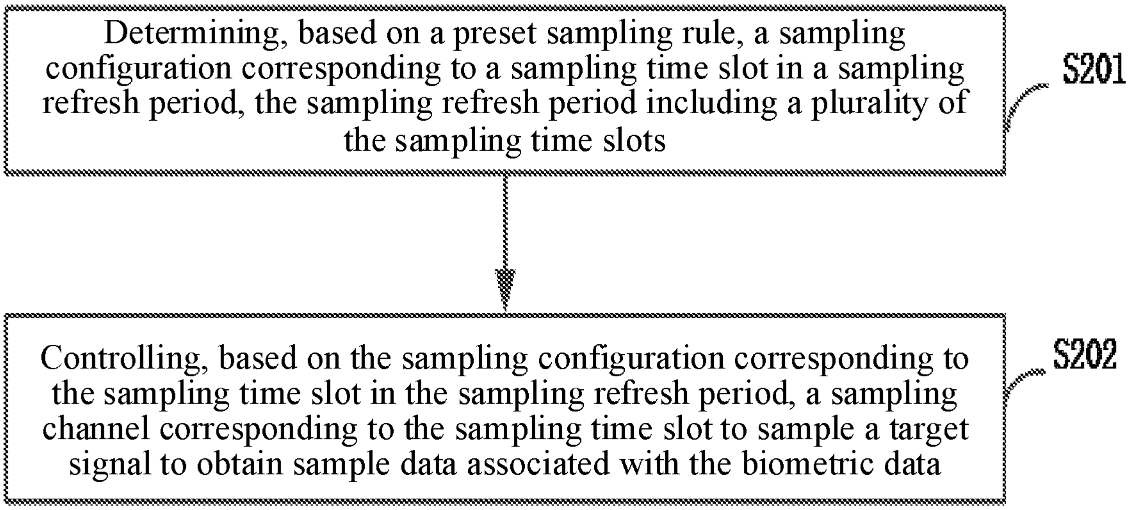
FIG. 2 is a schematic flowchart of a method for sampling biometric data in Embodiment II of the present disclosure.

FIG. 2 is a schematic flowchart of a method for sampling biometric data in Embodiment II of the present disclosure. As shown in FIG. 2, the method includes step S201 and step S202 below:

S201: determining, based on a preset sampling rule, a sampling configuration corresponding to a sampling time slot in a sampling refresh period, the sampling refresh period including a plurality of the sampling time slots.

Alternatively, in this embodiment, the preset sampling rule may include a sampling time slot configuration rule and a sampling configuration rule, the sampling time slot configuration rule may be used for setting a corresponding relationship between the sampling time slot and the sampling configuration, and the sampling configuration rule may be used for setting the sampling configuration, thereby fast determining the sampling configuration corresponding to the sampling time slot in the sampling refresh period when executing step S201.

Alternatively, in this embodiment, the sampling configuration may include a sampling channel enabling parameter and a sampling process control parameter, the sampling channel enabling parameter may be used for controlling switching on or off the corresponding sampling channel, and the sampling process control parameter may be used for setting a sampling parameter used by the corresponding sampling channel during sampling, thereby setting sampling configurations respectively for different sampling time slots in a same sampling channel when presetting the sampling rule, and improving the flexibility in sampling control process. When there is a plurality of sampling channels, sampling setting may be performed for different sampling time slots of different sampling channels, thereby improving the flexibility in sampling control process.

Alternatively, in this embodiment, the sampling parameter includes a sampling frequency relevant parameter and a data transceiving relevant parameter. Specifically, the sampling frequency relevant parameter includes, but is not limited to, the sampling refresh period, as long as a sampling frequency can be adjusted. The data transceiving relevant parameter includes, but is not limited to, any one parameter that can be used for adjusting a circuit connection relationship. An embodiment shown in FIG. 4A below may be referred to for example explanation on the sampling frequency relevant parameter and the data transceiving relevant parameter. Alternatively, in other embodiments, the sampling parameter may also merely include the sampling frequency relevant parameter and the data transceiving relevant parameter.

Alternatively, in this embodiment, the sampling configuration further includes a sampling configuration enabling parameter, and the sampling configuration enabling parameter is used for enabling or disabling the corresponding sampling configuration, thereby switching on or off a sampling channel corresponding to the sampling configuration, achieving the purpose of dynamically adjusting the switching on or off of the sampling channel, and reducing the power consumption.

S202: controlling, based on the sampling configuration corresponding to the sampling time slot in the sampling refresh period, a sampling channel corresponding to the sampling time slot to sample a target signal to obtain sample data associated with the biometric data.

Alternatively, in this embodiment, the controlling, based on the sampling configuration corresponding to the sampling time slot in the sampling refresh period, a sampling channel corresponding to the sampling time slot to sample a target signal to obtain sample data associated with the biometric data in step S202 specifically may include controlling, based on the sampling configuration corresponding to the sampling time slot in the sampling refresh period, the sampling channel corresponding to the sampling time slot to perform signal conversion on the target signal to obtain the sample data associated with the biometric data, thereby facilitating effectively implementing a specific application mode in a specific application scenario based on the sample data, e.g., wearing detection or biometric detection.

Further, in this embodiment, the controlling, based on the sampling configuration corresponding to the sampling time slot in the sampling refresh period, a sampling channel corresponding to the sampling time slot to sample a target signal to obtain sample data associated with the biometric data in step S202 specifically includes controlling, based on the sampling configuration corresponding to the sampling time slot in the sampling refresh period, a signal converter in the sampling channel corresponding to the sampling time slot to convert the target signal from a first analog form into a second analog form, and controlling an analog-to-digital converter in the sampling channel corresponding to the sampling time slot to perform analog-to-digital conversion on the target signal in the second analog form to obtain a corresponding digital signal, thereby facilitating effectively implementing the specific application mode in the specific application scenario based on the sample data.

Alternatively, in another embodiment, the sampling channel has a channel identifier, and the sampling configuration has a configuration identifier. Therefore, after the above step S202, a data packet header is configured for the sample data collected by the sampling channel, the data packet header includes the channel identifier of the sampling channel and the configuration identifier of the sampling configuration corresponding to the sampling channel, thereby implementing a sampling channel identifying the sample data and the employed sampling configuration, and achieving effective management of data.

Alternatively, in another embodiment, one of the sampling time slots is provided with a sampling period correspondingly, and before step S201, the method may further include: determining, based on a preset sampling refresh period, whether the sampling time slot matches a corresponding sampling period, and executing a step of determining the sampling configuration corresponding to the sampling time slot in the sampling refresh period based on the preset sampling rule when the sampling time slot matches the corresponding sampling period, thereby further improving the flexibility in sampling process control. For example, in some specific application scenarios, switching to different application modes is set, and different application modes have different sampling configurations, e.g., different sampling frequencies. Whether the sampling time slot matches the corresponding sampling period is determined based on the preset sampling refresh period, thereby realizing switching between sampling configurations corresponding to different application modes.

Alternatively, in another embodiment, the sampling refresh period is in an integral multiple relationship with the sampling period. Specifically, for example, the sampling refresh period is integer number times of the refresh period, thereby determining whether the sampling time slot matches the corresponding sampling period based on the refresh period, and further increasing the flexibility in sampling process control.

Alternatively, in another embodiment, before step S202, the method may further include: intercommunicating the sampling channel corresponding to the sampling time slot with a detection channel outputting the target signal based on a preset application mode, thereby realizing switching between different sampling configurations corresponding to different application modes.

Further, in another embodiment, the intercommunicating the sampling channel corresponding to the sampling time slot with a detection channel outputting the target signal based on a preset application mode may specifically include: intercommunicating the sampling channel corresponding to the sampling time slot with the detection channel outputting the target signal based on the preset application mode. A switch matrix in this step may be, e.g., a second switch matrix in an embodiment of FIG. 4A below. However, it should be noted that the sampling channel corresponding to the sampling time slot may be intercommunicated with the detection channel outputting the target signal in other ways in addition to the switch matrix.

Figure 3:
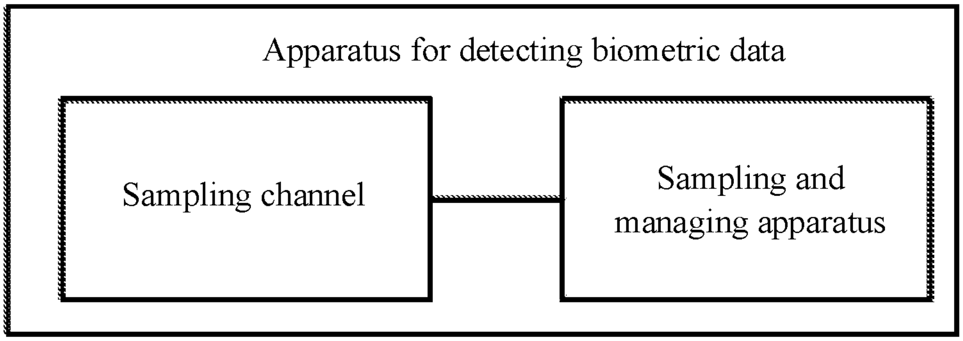
FIG. 3 is a schematic structural diagram of a circuit for sampling biometric data in Embodiment III of the present disclosure.

Corresponding to the method for sampling biometric data shown in FIG. 2, FIG. 3 provides a schematic structural diagram of an apparatus for detecting biometric data. Specifically, FIG. 3 is a schematic structural diagram of an apparatus for detecting biometric data in Embodiment III of the present disclosure. As shown in FIG. 3, the apparatus includes: a sampling and managing apparatus and a sampling channel. The sampling and managing apparatus is configured to determine, based on a preset sampling rule, a sampling configuration corresponding to a sampling time slot in a sampling refresh period, the sampling refresh period including a plurality of the sampling time slots; and the sampling and managing apparatus is configured to control, based on the sampling configuration corresponding to the sampling time slot in the sampling refresh period, the sampling channel corresponding to the sampling time slot to sample a target signal to obtain sample data associated with the biometric data.

In this embodiment, the sampling and managing apparatus specifically may include: a determining unit and a controlling unit (not shown in FIG. 3). The determining unit is configured to determine, based on the preset sampling rule, the sampling configuration corresponding to the sampling time slot in the sampling refresh period, the sampling refresh period including the plurality of sampling time slots; and the controlling unit is configured to control, based on the sampling configuration corresponding to the sampling time slot in the sampling refresh period, the sampling channel corresponding to the sampling time slot to sample the target signal to obtain the sample data associated with the biometric data.

Alternatively, in this embodiment, the preset sampling rule includes a sampling time slot configuration rule and a sampling configuration rule, the sampling time slot configuration rule is used for setting a corresponding relationship between the sampling time slot and the sampling configuration, and the sampling configuration rule is used for setting the sampling configuration, thereby fast determining the sampling configuration corresponding to the sampling time slot in the sampling refresh period.

Alternatively, in this embodiment, the sampling configuration includes a sampling channel enabling parameter and a sampling process control parameter, the sampling channel enabling parameter is used for controlling switching on or off the corresponding sampling channel, and the sampling process control parameter is used for setting a sampling parameter used by the corresponding sampling channel during sampling, thereby setting sampling configurations respectively for different sampling time slots in a same sampling channel when presetting the sampling rule, and improving the flexibility in sampling control process. When there is a plurality of sampling channels, sampling setting may be performed for different sampling time slots of different sampling channels, thereby improving the flexibility in sampling control process.

Alternatively, in this embodiment, the sampling parameter includes a sampling frequency relevant parameter and a data transceiving relevant parameter. Specifically, the sampling frequency relevant parameter includes, but is not limited to, the sampling refresh period, as long as a sampling frequency can be adjusted. The data transceiving relevant parameter includes, but is not limited to, any one parameter that can be used for adjusting a circuit connection relationship. An embodiment shown in FIG. 4A below may be referred to for example explanation on the sampling frequency relevant parameter and the data transceiving relevant parameter. In other embodiments, the sampling parameter may also merely include the sampling frequency relevant parameter and the data transceiving relevant parameter.

Alternatively, in another embodiment, the sampling configuration further includes a sampling configuration enabling parameter, and the sampling configuration enabling parameter is used for enabling or disabling the corresponding sampling configuration, thereby switching on or off the sampling channel corresponding to the sampling configuration, achieving the purpose of dynamically adjusting the switching on or off of the sampling channel, and reducing the power consumption.

Alternatively, in another embodiment, the sampling channel has a channel identifier, and the sampling configuration has a configuration identifier. The sampling and managing apparatus further includes a data packing unit (not shown in FIG. 3) configured to configure a data packet header for the sample data collected by the sampling channel, the data packet header includes the channel identifier of the sampling channel and the configuration identifier of the sampling configuration corresponding to the sampling channel, thereby implementing a sampling channel identifying the sample data and the employed sampling configuration, and achieving effective management of data.

Alternatively, in another embodiment, the sampling and managing apparatus further includes a determining unit (not shown in FIG. 3) configured to determine, based on a preset sampling refresh period, whether the sampling time slot matches a corresponding sampling period. The sampling and managing circuit determines the sampling configuration corresponding to the sampling time slot in the sampling refresh period based on the preset sampling rule when the sampling time slot matches the corresponding sampling period, thereby further improving the flexibility in sampling process control.

Specifically, in another embodiment, the sampling refresh period is in an integer multiple relationship with the sampling period, thereby determining whether the sampling time slot matches the corresponding sampling period based on the refresh period, thereby further increasing the flexibility in sampling process control.

Alternatively, in another embodiment, the sampling and managing apparatus further includes: an application mode switching unit (not shown in FIG. 3) configured to intercommunicate the sampling channel corresponding to the sampling time slot with a detection channel outputting the target signal based on a preset application mode, thereby realizing switching between different sampling configurations corresponding to different application modes.

Alternatively, in another embodiment, the sampling and managing apparatus further includes a switch matrix; and the application mode switching unit is further configured to intercommunicate the sampling channel corresponding to the sampling time slot with the detection channel outputting the target signal based on the preset application mode.

Alternatively, in another embodiment, the sampling and managing apparatus further includes: a converting unit (not shown in FIG. 3) configured to control, based on the sampling configuration corresponding to the sampling time slot in the sampling refresh period, the sampling channel corresponding to the sampling time slot to perform signal conversion on the target signal to obtain the sample data associated with the biometric data, thereby facilitating effectively implementing a specific application mode in a specific application scenario based on the sample data.

Further, in another embodiment, the converting unit includes a signal converter and an analog-to-digital converter. The signal converter is configured to control, based on the sampling configuration corresponding to the sampling time slot in the sampling refresh period, the signal converter in the sampling channel corresponding to the sampling time slot to convert the target signal from a first analog form into a second analog form, and the analog-to-digital converter is configured to perform analog-to-digital conversion on the target signal in the second analog form to obtain a corresponding digital signal, thereby facilitating effectively implementing a specific application mode in a specific application scenario based on the sample data.

In the following embodiments of the present disclosure, description is provided specifically with the sample data being PPG data as an example. Therefore, the target signal may be photoplethysmography, and the PPG data is used for detecting biometrics, e.g., heart rate. However, it should be noted that, for those of ordinary skills in the art, the technical solutions of the embodiments of the present disclosure can be applied to any scenario that requires biometric data sampling without departing from the technical solutions of the present disclosure.

In addition, in the following embodiments of the present disclosure, description is provided specifically with multi-channel sampling as an example. However, it should be noted that, for those of ordinary skills in the art, the technical solutions of the embodiments of the present disclosure can also be applied to an application scenario of single-channel sampling without departing from the technical solutions of the present disclosure.

The sampling and managing apparatus provided in the above embodiments may be implemented by hardware, or may be implemented by software.

Figure 4A:
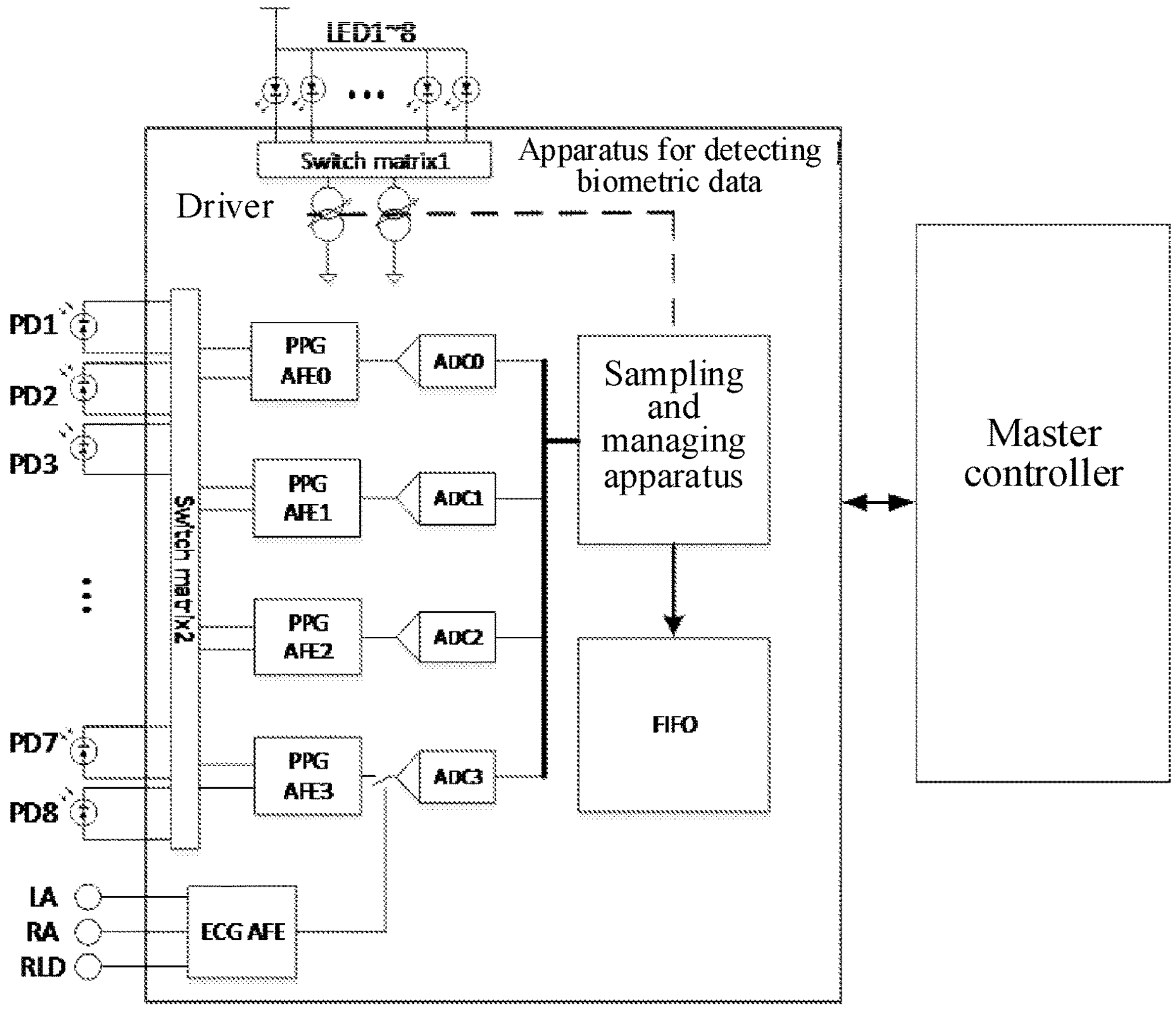
FIG. 4A is a schematic diagram of an apparatus for detecting biometric data in Embodiment IV of the present disclosure.

FIG. 4A is a schematic diagram of an apparatus for detecting biometric data in Embodiment IV of the present disclosure. As shown in FIG. 4A, description is provided with simultaneous detection of heart rate and electrocardiogram (ECG for short) as an example, and description is provided with heart rate detection, e.g., by photoplethysmography (PPG for short) and multi-channel as an example. The apparatus for detecting biometric data includes a driver, a signal detecting circuit, a sampling and managing apparatus for biometric data, a PPG Analog Front End, an ECG Analog Front End, and an analog-to-digital converter. The driver is mainly configured to drive the signal detecting circuit. The signal detecting circuit is mainly configured to detect the target signal (specifically including a target signal that can reflect heart rate, i.e., a PPG signal, and a target signal that can reflect electrocardiogram, i.e., an ECG signal, in this embodiment). For heart rate detection, the PPG Analog Front End is mainly configured to perform signal conversion on the target signal, e.g., converting a voltage signal into a current signal. The analog-to-digital converter is configured to perform analog-to-digital conversion on an output of the PPG Analog Front End to obtain sample data. For electrocardiogram detection, the ECG Analog Front End samples the target signal that can reflect electrocardiogram, and the analog-to-digital converter is configured to perform analog-to-digital conversion on an output of the ECG Analog Front End to obtain sample data. The master controller is mainly configured to control the apparatus for detecting biometric data, and is configured to compute heart rate based on the sample data that can reflect heart rate and form electrocardiogram based on the sample data that can reflect electrocardiogram in some specific application scenarios. Here, description is provided with the apparatus for detecting biometric data that does not include the master controller as an example. However, in other embodiments, the apparatus for detecting biometric data may also include the master controller.

Specifically, in this embodiment, the signal detecting circuit may include 8 light-emitting diodes (denoted as LED1 to LED8 successively), 8 photodiodes (denoted as PD1 to PD8 successively), and 2 drivers (denoted as LED Driver1 and LED Driver2 respectively), and a first switch matrix (denoted as switch matrix1). The first switch matrix is configured to establish an electrical connection between the light-emitting diode and the driver, such that the driver drives the light-emitting diode to emit light. The light-emitting diode is configured to provide light irradiated to a human body under the drive of the driver. The photodiode is configured to sense light that is emitted by the light-emitting diode and is processed (transmitted or reflected) by and sent out from the human body, and generate the target signal. Generally, the target signal is the voltage signal. A light-emitting diode and a photodiode can form a detection channel. Here, it should be noted that the light-emitting diode and the photodiode may not be provided on the apparatus for detecting biometric data, as long as they can actually constitute the signal detecting circuit. Further, in other embodiments, the apparatus for detecting biometric data may not include the signal detecting circuit, or in other words, the signal detecting circuit may be provided on another external circuit structure.

Preferably, within one corresponding sampling refresh period, one driver can drive 4 light-emitting diodes to emit light. Correspondingly, 4 photodiodes sense light that is emitted by the light-emitting diodes and is processed (transmitted or reflected) by and sent out from a human body, and generate a target signal.

Specifically, in this embodiment, the apparatus for detecting biometric data includes: 4 PPG Analog Front Ends (PPG AFE for short) (denoted as PPG AFE0 to PPG AFE3 successively), 4 Analog-to-Digital Converters (ADC for short) (denoted as ADC0 to ADC3 successively), a second switch matrix (denoted as switch matrix2), 1 ECG Analog Front End (ECG AFE for short), a sampling and managing apparatus, and a buffer circuit, e.g., a First Input First Output (FIFO for short). The First Input First Output (FIFO) is mainly configured to buffer the sample data, such that the master controller acquires the sample data, thereby reducing the access burden of the master controller.

In this embodiment, for the sampling of the target signal that can reflect heart rate, a sampling channel includes a PPG Analog Front End and an analog-to-digital converter. The second switch matrix is configured to establish an electrical connection between the PPG Analog Front End and the light-emitting diode to establish the sampling channel; the PPG Analog Front End is configured to perform signal conversion on the target signal, e.g., converting the voltage signal into the current signal, and the analog-to-digital converter is configured to perform analog-to-digital conversion on the output of the PPG Analog Front End to obtain the sample data.

Preferably, in this embodiment, for the sampling of the target signal that can reflect heart rate, 8 sampling channels (with channel identifiers 0, 1, 2, 3, 5, 6, 7, and 8 respectively) are arranged totally within one corresponding sampling refresh period. For each sampling channel, a photodiode is connected to a PPG Analog Front End, and a PPG Analog Front End is connected to an analog-to-digital converter.

Further, in this embodiment, for the sampling of the target signal that can reflect heart rate, the ECG Analog Front End is connected to one of the above analog-to-digital converters, i.e., an analog-to-digital converter can be multiplexed for the sampling of the target signal that can reflect heart rate and the sampling of the target signal that can reflect ECG. Specifically, for example, a selector switch is used for multiplexing an analog-to-digital converter. In this embodiment, the ECG Analog Front End (ECG AFE) is driven based on a potential difference between a left arm (LA for short) and a right arm, and a right leg driver (RLD for short). An electrode connected to the left arm is referred to as a LA electrode, an electrode connected to the right arm is referred to as a RA electrode, and an electrode connected to the right leg is referred to as a RLD electrode. Therefore, when the ECG Analog Front End (ECG AFE) is sampling, output signals of the LA electrode, the RA electrode, and the RLD electrode are used as target signals, and the corresponding sample data is referred to as ECG data.

Description is provided with an application in a specific scenario as an example. For example, each photodiode senses light that is emitted by the light-emitting diode and is processed (transmitted or reflected) by and sent out from the human body, and generates a target signal. Based on an effective duration for which the light-emitting diode is driven, a sampling refresh period is divided into 8 sampling time slots (denoted as Timeslot 0 to Timeslot 7 respectively, Ts0 to Ts7 for short). Therefore, a time slot configuration rule and a sampling configuration rule included in a preset sampling rule are shown in Table I and Table II below respectively. For example, the time slot configuration rule and the sampling configuration rule may be specifically embodied as a time slot configuration table and a sampling configuration table, respectively.

TABLE I

| Time Slot Configuration Rule | | | | | |
|---|---|---|---|---|---|
| | Timeslot | | | | |
| | Ts0 | Ts1 | Ts2 | | Ts7 |
| Duration<br>SampleCfg | | | | . . . | |

In the above Table I, Timeslot represents a slot identifier for a sampling time slot (denoted as Ts0 to Ts7 successively), Duration represents a time length occupied by a sampling time slot, which is equal to an effective time length for which the light-emitting diodes Led1 to LED are driven respectively (or also known as a lighting duration), and SampleCfg represents a configuration identifier for a sampling configuration (denoted as SampleCfg0 to SampleCfg7 successively).

TABLE II

| Sampling Configuration Rule | | | | | | |
|---|---|---|---|---|---|---|
| Configuration identifier | Sampling configuration enabling parameter | Sampling channel enabling parameter (ECG enabling) | Sampling channel enabling parameter (ADC enabling) | Sampling frequency relevant parameter (sampling refresh period) | Data transceiving relevant parameter (Tx parameter) | Data transceiving relevant parameter (Rx parameter) |
| SampleCfg0 | | | | | | |
| SampleCfg1 | | | | | | |
| SampleCfg2 | | | | | | |
| . . . | | | | | | |
| SampleCfg7 | | | | | | |

Referring to the above Table II, the sampling configuration includes the sampling configuration enabling parameter, the sampling channel enabling parameter, and the sampling process control parameter.

In this embodiment, the sampling configuration enabling parameter is used for enabling or disabling the corresponding sampling configuration. Only when the sampling configuration corresponding to the sampling time slot is in an enabled state, can a corresponding sampling channel use the corresponding sampling channel enabling parameter and the sampling process control parameter during sampling, i.e., sampling the target signal within the sampling time slot; otherwise, when the sampling configuration corresponding to the sampling time slot is in a disabled state, the corresponding sampling channel cannot use the corresponding sampling channel enabling parameter or the sampling process control parameter during sampling, and stops sampling the target signal within the sampling time slot. Thus it can be seen that the corresponding sampling channel can be switched on or off in any sampling time slot through the sampling configuration enabling parameter, thereby realizing the flexibility in sampling process control on the one hand. On the other hand, the corresponding sampling configuration can be dynamically adjusted to be switched on or off through the sampling configuration enabling parameter, e.g., one or more sampling configurations of the above configuration identifiers SampleCfg0 to SampleCfg7 in FIG. 4A are dynamically adjusted to be switched on or off, thereby reducing the power consumption; or, the corresponding sampling configuration is always in an off state through the sampling configuration enabling parameter, for example, one or more sampling configurations of the above configuration identifiers SampleCfg0 to SampleCfg7 in FIG. 4A are always in an off state, thereby further reducing the power consumption.

Further, on the basis of the above configuration identifiers SampleCfg0 to SampleCfg7, a sampling suspension configuration identifier SampleCfg8 may also be additionally provided. During sampling of a current sampling period, the sampling suspension configuration identifier is loaded to suspend the sampling of the current sampling period and wait for a next sampling period to continue sampling.

In this embodiment, the sampling channel enabling parameter is used for controlling switching on or off the corresponding sampling channel. For example, in FIG. 4A, the sampling channel enabling parameter includes an ECG sampling channel enabling parameter (ECG enabling parameter for short) and a heart rate sampling channel enabling parameter (represented by an ADC enabling parameter). Through the ECG sampling channel enabling parameter, an ECG sampling channel can be switched on to sample the ECG signal or switched off to stop sampling the ECG signal. Through the heart rate sampling channel enabling parameter, one or more heart rate sampling channels can be switched on to sample a photodiode output signal or switched off to stop sampling the photodiode output signal, thereby realizing the flexibility in sampling process control on the one hand.

In addition, when pre-configuring the above sampling rule, different sampling frequencies may be set for different heart rate sampling channels or different sampling time slots of a same heart rate sampling channel based on different application modes. For example, for a smart bracelet or a smart earphone, the application mode may include wearing detection and heart rate detection. The wearing detection is mainly used for determining whether a user is wearing a smart bracelet or a smart earphone, while the heart rate detection is mainly used for computing heart rate of a user, so as to provide, e.g., health or exercise suggestions.

Further, in some application scenarios, if a new application mode is required to be additionally provided, based on the sampling time slot configuration rule and the sampling configuration rule mentioned above, it is only necessary to directly improve at least one of the sampling configuration enabling parameter of the sampling time slot in the sampling configuration rule, the sampling channel enabling parameter, or the sampling process control parameter, thereby improving the flexibility in sampling process control on the one hand. For example, when the pre-configured original sampling rule is only for the application mode of heart rate detection, the application mode of wearing detection is additionally required in some application scenarios. Therefore, it is only necessary to modify a part of the sampling configurations in the sampling configuration rule. For example, a sampling frequency may be changed by modifying the sampling frequency relevant parameter, and a connection mode of the driver and the light-emitting diode may be modified through the data transceiving relevant parameter. For example, the sampling configuration corresponding to the configuration identifier SampleCfg0 is modified to implement 5 Hz red light PPG sampling, so as to adapt to wearing detection; and the sampling configurations corresponding to the configuration identifiers SampleCfg1 and SampleCfg2 are modified to implement 25 Hhz green light PPG sampling, so as to adapt to heart rate detection.

The sampling process control parameter is used for setting a sampling parameter used by the corresponding sampling channel during sampling, the sampling parameter may include the sampling frequency relevant parameter (e.g., the sampling refresh period), the data transceiving relevant parameter (e.g., a data receiving parameter (Rx parameter for short) and a data transmitting parameter (Tx parameter for short)), and the sampling frequency relevant parameter may be used for setting a sampling frequency for each sampling time slot, thereby achieving different sampling channels with different sampling frequencies. The data transceiving relevant parameter can be used for setting the connection mode of the light-emitting diode and the driver, and a drive current of the light-emitting diode through the first switch matrix, and setting a connection between the photodiode and the PPG Analog Front End through the second switch matrix, circuit parameters of the PPG Analog Front End (e.g., gain, compensation capacitor size), and circuit parameters of the analog-to-digital converter (e.g., the number of times of oversampling), thereby realizing the flexibility in sampling process control on the one hand.

In addition, the sampling and managing apparatus causes a weak coupling relationship between a sampling control process and the master controller. Therefore, the sampling control process not only can realize the flexibility in sampling process control, but also can reduce the burden of the master controller, compared with existing technologies.

Further, in some other embodiments, the sampling and managing apparatus further includes a data packing unit configured to configure a data packet header for the sample data collected by the sampling channel, the data packet header includes the channel identifier of the sampling channel and the configuration identifier of the sampling configuration corresponding to the sampling channel, thereby implementing a sampling channel identifying the sample data and the employed sampling configuration, and achieving effective management of data.

Further, in some other embodiments, the data packet header may also include an assistant marker, which is used for marking additional information of the sampling control process, for example, whether dimming is involved in the sampling control process, i.e., brightness adjustment of the light-emitting diode. For example, in an application scenario, when a data packet header is configured for the sample data based on the sampling time slot configuration rule and the sampling configuration rule provided in FIG. 4A, and the data packet header includes the channel identifier of the sampling channel, the configuration identifier of the sampling configuration corresponding to the sampling channel, and the assistant marker data, the sample data may occupy 24 bits, one configuration identifier may occupy 3 bits, one channel identifier may occupy 2 bits, and the assistant marker may occupy 3 bits. Thus, the sample data and the data packet header include 32 bits in total.

Alternatively, in another embodiment, the sampling and managing apparatus may further include a determining unit configured to determine, based on a preset sampling refresh period, whether the sampling time slot matches a corresponding sampling period. The sampling and managing apparatus determines the sampling configuration corresponding to the sampling time slot in the sampling refresh period based on the preset sampling rule when the sampling time slot matches the corresponding sampling period, thereby further improving the flexibility in sampling process control. For example, whether the sampling time slot matches the corresponding sampling period is determined based on the preset sampling refresh period, thereby realizing switching between sampling configurations corresponding to different application modes. In this embodiment, for example, wearing detection is switched to heart rate detection.

An implementation form of the apparatus for detecting biometric data in the above embodiments may be flexibly selected, which may be implemented in the form of a chip or in other forms.

Figure 4B:
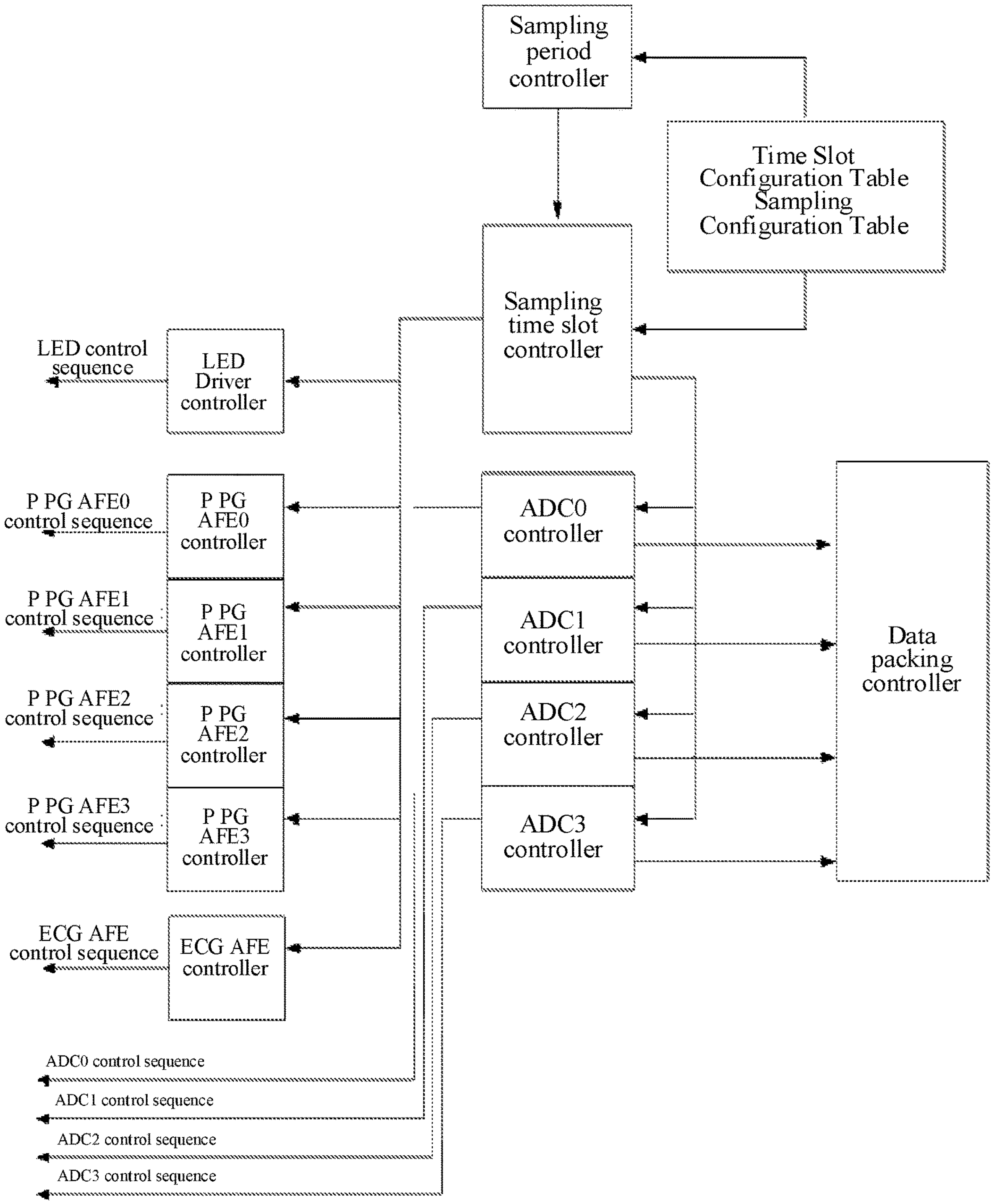
FIG. 4B is a schematic structural diagram of the sampling and managing apparatus for biometric data in FIG. 4A implemented by hardware.

FIG. 4B is a schematic structural diagram of the sampling and managing apparatus for biometric data in FIG. 4A implemented by hardware. For example, FIG. 4B provides a structure of an apparatus for managing biometric data, which may include: a sampling refresh period controller, a sampling time slot controller, 4 PPG Analog Front End controllers (denoted as PPG AFE0 controller to PPG AFE3 controller successively in FIG. 4B), 4 Analog-to-Digital Converter controllers (denoted as ADC0 controller to ADC3 controller successively in FIG. 4B), and 1 ECG Analog Front End controller (denoted as ECG AFE controller in FIG. 4B). The PPG AFE0 controller to PPG AFE3 controller and the ECG AFE controller are equivalent to the above controlling unit, where:

the sampling refresh period controller is configured to control the sampling refresh period;

the sampling time slot controller is configured to read the time slot configuration rule and the sampling configuration rule in units of the sampling refresh period under the control of the sampling refresh period controller, and generate trigger pulses of a LED driver controller, PPG0 controller to PPG3 controller, an ECG AFE controller, and ADC0 controller to ADC3 controller; and the determining unit may be specifically configured on the time judgment controller.

The LED driver controller is configured to sample corresponding trigger pulses and generate a LED driver control sequence to control a LED driving unit to drive or stop driving a LED;

the PPG AFE 0 controller to PPG AFE3 controller sample corresponding trigger pulses, and generate PPG AFE0 control sequence to PPG AFE3 control sequence to control the PPG AFE0 to PPG AFE3 to start or stop running; and the ECG AFE controller samples corresponding trigger pulses and generates an ECG AFE control sequence to control the ECG AFE to start or stop working.

The ADC0 controller to ADC3 controller sample corresponding trigger pulses, and generate ADC0 control sequence to ADC3 control sequence to control the ADC0 to ADC3 to start or stop running; and a data packing controller is configured to configure a data packet header for the collected sample data under the control of the ADC 0 controller to ADC3 controller (this process may be referred to as data packing), and transfer the sample data to a FIFO for storage. The data packing unit may be specifically configured on the data packing controller.

Figure 5:
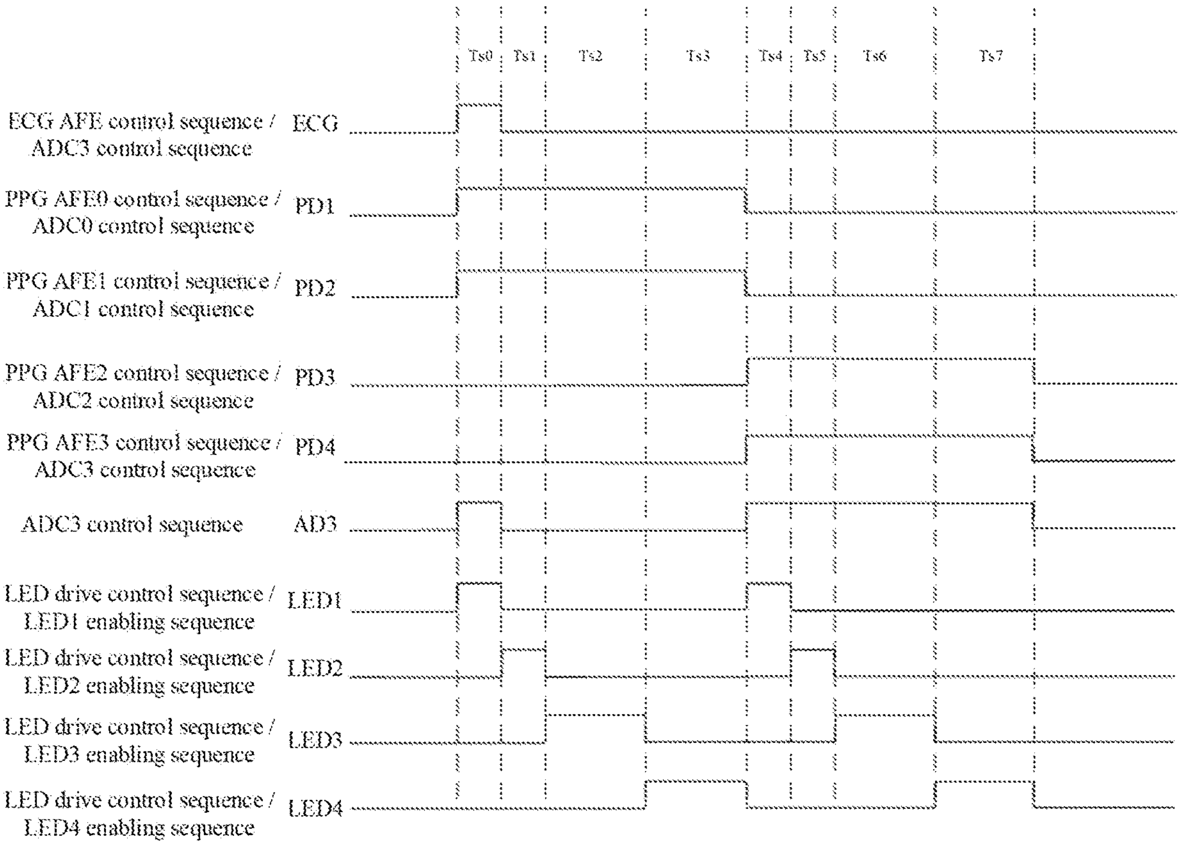
FIG. 5 is a sequence diagram of a sampling control process in Embodiment V of the present disclosure.

FIG. 5 is a sequence diagram of a sampling control process in Embodiment V of the present disclosure. As shown in FIG. 5, description is provided with the sampling time slots Ts0 to Ts3 and corresponding sampling configurations SampleCfg0 to SampleCfg3 thereof as an example. Specifically, in the sampling time slot Ts0, first, an ECG AFE is controlled, enabled and driven to sample a target signal that can reflect ECG based on an ECG AFE control sequence generated by an ECG AFE controller. At the same time, an ECG AFE is electrically connected to the ADC3 through a selector switch. At the same time, the ADC3 is controlled to perform analog-to-digital conversion on an output signal generated by the ECG AFE based on an ADC3 control sequence generated by an ADC3 controller, to obtain corresponding sample data. In this case, because the PD3 is not working, the PPG AFE3 is controlled not to detect a target signal generated by the PD3 based on a PPG AFE3 control sequence generated by a PPG AFE3 controller. In the sampling time slot Ts0, a LED driver controller generates a LED control sequence to control a LED driver to drive the light-emitting diode LED1 to be lightened, and a PPG AFE0 controller generates a PPG AFE0 control sequence to control the PPG AFE0 to collect a target signal generated by the photodiode PD1. At the same time, an ACD0 controller generates an ADC0 control sequence to control the ADC0 to perform analog-to-digital conversion on an output signal generated by the PPG AFE0, to obtain corresponding sample data. Similarly, a PPG AFE1 controller generates a PPG AFE1 control sequence to control the PPG AFE1 to collect a target signal generated by the photodiode PD2; and then in the sampling time slots Ts1, Ts2, and Ts3 in sequence, a LED driver controller generates a LED control sequence to control the LED driver to drive the light-emitting diodes LED2, LED3, and LED4 to be lightened in sequence. The PPG AFE0 controller generates the PPG AFE0 control sequence to control the PPG AFE0 to continue collecting the target signal generated by the photodiode PD1, and the PPG AFE1 controller generates the PPG AFE1 control sequence to control the PPG AFE1 to continue collecting the target signal generated by the photodiode PD2. Then, the light-emitting diodes LED1 to LED4 are lightened again by an approach identical to the previous approach. The differences are that, on the one hand, the ECG AFE stops sampling, and on the other hand, the PPG AFE2 collects the target signal generated by the photodiode PD3, while the PPG AFE3 collects a target signal generated by the photodiode PD4. The target signals collected by the PPG AFE0 to the PPG AFE3 are subjected to analog-to-digital conversion respectively by the analog-to-digital converters ADC0 to ADC3 to obtain sample data. The sample data is buffered in the First Input First Output (FIFO) shown in FIG. 4A, such that the controllers acquire the sample data, thereby reducing the access burden of the controllers.

Similarly, for the sampling time slots Ts4 to Ts7 corresponding to the sampling configurations SampleCfg4 to SampleCfg7, the light-emitting diodes LED1 to LED4 are replaced with the light-emitting diodes LED5 to LED7. For the sampling time slots Ts0 to Ts3, the PPG AFE0 continues collecting a target signal generated by the photodiode PD5, and the PPG AFE1 continues collecting a target signal generated by the photodiode PD6. For the sampling time slots Ts4 to Ts7, the PPG AFE2 continues collecting a target signal generated by the photodiode PD7, and the PPG AFE3 continues collecting a target signal generated by the photodiode PD8. The target signals collected by the PPG AFE0 to the PPG AFE3 are subjected to analog-to-digital conversion respectively by the analog-to-digital converters ADC0 to ADC3 to obtain sample data. Here, in the sampling time slot Ts4, the PPG AFE3 is electrically connected to the ADC3 through the above selector switch.

As can be seen from FIG. 5, for each sampling channel, sampling may be performed based on 8 sampling configurations that are set based on sampling time slots within one sampling refresh period. Similarly, sampling may be performed based on less than 8 or more than 8 sampling configurations that are set based on sampling time slots within one sampling refresh period, thereby improving the flexibility in sampling control process.

An embodiment of the present disclosure further provides a chip configured to implement the above apparatus for detecting biometric data. The apparatus for detecting biometric data includes a sampling channel and a sampling and managing apparatus. Preferably, the sampling channel may include a driver, a PPG Analog Front End, an analog-to-digital converter, a first switch matrix, a second switch matrix, an ECG Analog Front End, a sampling and managing apparatus, and a buffer circuit.

In other embodiments, the sampling channel may further include at least one of a light-emitting diode or a photodiode.

The above product can execute the method provided in embodiments of the present disclosure, and has corresponding function modules for executing the method and beneficial effects. The method provided in the embodiments of the present disclosure may be referred to for the technical details that are not described in detail in this embodiment.

So far, specific embodiments of the present subject matter have been described. Other embodiments fall within the scope of the appended claims. In some cases, actions disclosed in the appended claims may be performed in different orders and can still achieve the desired results. In addition, the processes depicted in the figures do not necessarily require the shown particular order or sequential order, to achieve the desired results. In some embodiments, multitasking and parallel processing may be advantageous.

In the 1990s, an improvement of a technology can be clearly distinguished between a hardware improvement (e.g., an improvement on a circuit structure of a diode, a transistor, a switch, or the like) or a software improvement (e.g., an improvement on a process). However, with the development of the technology, at present, improvements of many processes can be regarded as direct improvements of a hardware circuit structure. Almost all designers obtain a corresponding hardware circuit structure by programming the improved process into a hardware circuit. Therefore, it cannot be said that an improvement of a process cannot be implemented with hardware entity modules. For example, a programmable logic device (PLD) (e.g., a Field Programmable Gate Array (FPGA)) is such an integrated circuit that its logical functions are determined by a user through programming a device. A designer "integrates" a digital system onto a PLD by programming by himself without requiring a chip manufacturer to design and manufacture a dedicated integrated circuit chip. Further, at present, instead of manually making integrated circuit chips, this kind of programming is mostly implemented by using "logic compiler" software, which is similar to a software compiler used in program development and compilation. The previous original code must also be compiled in a specific programming language, which is referred to as Hardware Description Language (HDL), and there is not only one kind, but many kinds of HDL, e.g., ABEL (Advanced Boolean Expression Language), AHDL (Altera Hardware Description Language), Confluence, CUPL (Cornell University Programming Language), HDCal, JHDL (Java Hardware Description Language), Lava, Lola, MyHDL, and PALASM, RHDL (Ruby Hardware Description Language). At present, VHDL (Very-High-Speed Integrated Circuit Hardware Description Language) and Verilog are most commonly used. Those skilled in the art should further clearly know that it will be very easy to obtain a hardware circuit that implements the logical process only by slightly logically programming the process with the above hardware description languages and programming the process into an integrated circuit.

The controller can be implemented in any suitable manner. For example, the controller may take the form of a microprocessor or a processor and a computer-readable medium storing computer-readable program code (such as software or firmware) executable by the (micro)processor, a logic gate, a switch, an application specific integrated circuit (ASIC), a programmable logic controller, and an embedded microcontroller. Examples of the controller include, but are not limited to, the following microcontrollers: ARC 625D, Atmel AT91SAM, Microchip PIC18F26K20, and Silicone Labs C8051F320. A memory controller can also be implemented as a part of the memory control logic. Those skilled in the art also know that in addition to implementing the controller in a manner of purely computer-readable program code, it is completely possible to logically programme the process such that the controller implements a same function in the form of a logic gate, a switch, an application specific integrated circuit, a programmable logic controller, an embedded microcontroller, or the like. Therefore, such a controller can be regarded as a hardware component, and an apparatus included therein and configured to implement various functions can also be regarded as a structure within the hardware component. Or even, the apparatus configured to implement various functions may be regarded as not only a software module for implementing the method but also the structure within the hardware component.

The system, apparatus, modules or units illustrated in the above embodiments may be specifically implemented by a computer chip or entity, or by a product having a certain function. A typical implementing device is a computer. Specifically, the computer, e.g., may be a personal computer, a laptop computer, a cellular phone, a camera phone, a smart phone, a personal digital assistant, a medium player, a navigation device, an e-mail device, a game console, a tablet computer, a wearable device, or a combination of any device of these devices.

For ease of description, when the apparatus is described, the apparatus is divided into various units based on functions, and then the units are described respectively. Of course, when the present disclosure is implemented, the functions of the units can be implemented in a same piece or more pieces of software and/or hardware.

As will be appreciated by those skilled in the art, the embodiments of the present disclosure may be provided as a method, system, or computer program product. Accordingly, the present disclosure may take the form of an entirely hardware embodiment, an entirely software embodiment, or an embodiment combining software and hardware. Further, the present disclosure may take the form of a computer program product embodied in one or more computer-readable storage mediums (including, but not limited to, a disk memory, a CD-ROM, an optical memory, and the like) having computer-usable program code embodied thereon.

The present disclosure is described with reference to the flowcharts and/or block diagrams of the method, device (system), and computer program product according to the embodiments of the present disclosure. It should be understood that each process and/or block in the flow charts and/or block diagrams as well as combinations of processes and/or blocks in the flow charts and/or block diagrams may be implemented by computer program instructions. The computer program instructions may be provided to a processor of a general purpose computer, a special purpose computer, an embedded processor, or other programmable data processing devices to produce a machine, such that the instructions executed via the processor of the computer or other programmable data processing devices create an apparatus for implementing the functions specified in one or more processes in the flow charts and/or one or more blocks in the block diagrams.

These computer program instructions may also be stored in a computer-readable memory that can direct a computer or other programmable data processing devices to function in a particular manner, such that the instructions stored in the computer-readable memory produce an article of manufacture including an instruction apparatus which implements the functions specified in one or more processes in the flow charts and/or one or more blocks in the block diagrams.

The computer program instructions may also be loaded onto a computer or other programmable data processing devices, to cause a series of operational steps to be performed on the computer or other programmable devices, to produce a computer implemented process, such that the instructions executed on the computer or other programmable devices provide steps for implementing the functions specified in one or more processes in the flow charts and/or one or more blocks in the block diagrams.

In a typical configuration, a computing device includes one or more processors (CPU), an input/output interface, a network interface, and an internal memory.

The internal memory may include forms, such as a volatile memory, a random access memory (RAM), and/or a nonvolatile memory, e.g., a read-only memory (ROM) or a flash RAM, in a computer-readable medium. The internal memory is an example of the computer-readable medium.

The computer-readable medium includes permanent and non-permanent mediums, removable and non-removable mediums, and information storage can be implemented by any method or technology. The information may be a computer-readable instruction, a data structure, a program module, or other data. Examples of the computer storage medium include, but are not limited to, a phase-change random access memory (PRAM), a static random access memory (SRAM), a dynamic random access memory (DRAM), a random access memory (RAM) of other type, a read-only memory (ROM), an electrically erasable programmable read-only memory (EEPROM), a flash RAM or other internal memory technology, a compact disc read-only memory (CD-ROM), a digital versatile disc (DVD) or other optical storage, a magnetic cassette tape, and a magnetic tape or magnetic disk storage or other magnetic storage device, or any other non-transmission medium, which can be configured to store information accessible to the computing device. As defined herein, the computer-readable medium excludes transitory media, e.g., a modulated data signal or carrier wave.

It should be further noted that the terms such as "comprising", "including" or any other variation thereof are intended to cover non-exclusive inclusions, such that a process, method, article, or device that includes a series of elements not only includes those elements, but also includes other elements that are not explicitly listed, or further includes elements that are inherent to such process, method, article, or device. An element defined by the wording "comprises a . . . " does not, without more constraints, preclude the existence of additional identical elements in the process, method, article, or device that includes the element.

As will be appreciated by those skilled in the art, the embodiments of the present application may be provided as a method, system, or computer program product. Accordingly, the embodiments of the present application may take the form of an entirely hardware embodiment, an entirely software embodiment, or an embodiment combining software and hardware. Further, the present disclosure may take the form of a computer program product embodied in one or more computer-readable storage mediums (including, but not limited to, a disk memory, a CD-ROM, an optical memory, and the like) having computer-usable program code embodied thereon.

The present disclosure may be described in the general context of computer-executable instructions executed by a computer, e.g., program modules. Generally, the program modules include routines, programs, objects, components, data structures, etc. that perform specific tasks or implement specific abstract data types. The present disclosure may also be practiced in distributed computing environments. In these distributed computing environments, remote processing devices connected through a communication network execute tasks. In a distributed computing environment, the program modules may be located in local and remote computer storage mediums including storage devices.

The embodiments in the present specification are described progressively, identical or similar portions between the embodiments may be mutually referred to, and differences of each embodiment from other embodiments are mainly described in the embodiment. In particular, embodiments of the system are substantially similar to embodiments of the method, and therefore are relatively simply described. A part of description of the embodiments of the method may be referred to for relevant parts.

The above description merely provides embodiments of the present disclosure, and is not intended to limit the present disclosure. For those skilled in the art, the present disclosure may have various modifications and alterations. Any modification, equivalent replacement, improvement, and the like made within the spirit and principles of the present disclosure should be included within the scope of the appended claims of the present disclosure.

What is claimed is:

1. A method for sampling biometric data, comprising:

(a) determining, based on a preset sampling rule, a sampling configuration of a plurality of sampling configurations corresponding to a sampling time slot in a sampling refresh period, the sampling refresh period comprising a plurality of the sampling time slots; and (b) controlling, based on the sampling configuration corresponding to the sampling time slot in the sampling refresh period, a sampling channel of a plurality of sampling channels corresponding to the sampling time slot to sample a target signal to obtain sample data associated with the biometric data, wherein the method is applied to a sampling and managing apparatus for controlling the plurality of sampling channels to sample a target signal reflecting biometric data, each of the sampling channels comprising an analog front-end and an analog-to-digital converter connected to the analog front-end, the sampling and managing apparatus comprising a time slot configuration table, a sampling configuration table, a sampling refresh period controller, a sampling time slot controller, a controller of a LED driver, analog front-end controllers, and analog-to-digital converter controllers, wherein the time slot configuration table comprises a correspondence between slot identifiers for the plurality of sampling time slots and configuration identifiers for the plurality of sampling configurations, and the sampling configuration table comprises a correspondence between the configuration identifiers and the plurality of sampling configurations, each of the sampling configurations comprising a sampling channel enabling parameter and a sampling process control parameter, the sampling channel enabling parameter being used for switching on or off a sampling channel corresponding to the sampling configuration, and the sampling process control parameter being used for setting a sampling parameter used by the sampling channel corresponding to the sampling configuration during sampling, the (a) determining, based on a preset sampling rule, a sampling configuration corresponding to a sampling time slot in a sampling refresh period, comprises:

(a1) with the sampling refresh period controller, controlling a sampling refresh period, and controlling the sampling time slot controller to read the time slot configuration table and the sampling configuration table in units of the sampling refresh period, and (a2) with the sampling time slot controller, for each sampling time slot in the sampling refresh period, under the control of the sampling refresh period controller:

(a21) reading the time slot configuration table based on a slot identifier for the sampling time slot to determine a configuration identifier for a sampling configuration corresponding to the slot identifier, and (a22) reading the sampling configuration table based on the configuration identifier to determine the sampling channel enabling parameter and the sampling process control parameter corresponding to the sampling time slot, the (b) controlling, based on the sampling configuration corresponding to the sampling time slot in the sampling refresh period, a sampling channel corresponding to the sampling time slot to sample a target signal to obtain sample data associated with the biometric data, comprises:

(b1) generating trigger pulses for the controller of the LED driver, the analog front-end controllers and the analog-to-digital converter controllers, (b2) with the controller of the LED driver, sampling the trigger pulses for the LED driver and generate a LED driver control sequence to control a LED driving unit to drive or stop driving a LED, and (b3) with the analog front-end controllers, sampling the trigger pulses for the analog front-end controllers and generate analog front-end control sequences to control the analog front-ends to start or stop collecting a target signal from a respective photodiode, and (b4) with the analog-to-digital converter controllers, sampling the trigger pulses for the analog-to-digital converter controller and generate analog-to-digital converter control sequences to control the analog-to-digital converters to start or stop converting the collected target signal from the respective photodiode to corresponding sample data.

2. The method according to claim 1, wherein the sampling parameter comprises at least one of a sampling frequency relevant parameter or a data transceiving relevant parameter.

3. The method according to claim 1, wherein each of the sampling configurations further comprises a sampling configuration enabling parameter, and the sampling configuration enabling parameter is used for enabling or disabling the corresponding sampling configuration.

4. The method according to claim 1, wherein each of the sampling channels has a channel identifier; and after the controlling, based on the sampling configuration corresponding to the sampling time slot in the sampling refresh period, a sampling channel corresponding to the sampling time slot to sample a target signal to obtain sample data, the method comprises:

configuring a data packet header for the sample data collected by the sampling channel, the data packet header comprising the channel identifier of the sampling channel and the configuration identifier of the sampling configuration corresponding to the sampling channel.

5. The method according to claim 1, wherein one of the sampling time slots corresponds to a sampling period, and before the determining, based on a preset sampling rule, a sampling configuration corresponding to a sampling time slot in a sampling refresh period, the method comprises:

determining, based on a preset sampling refresh period, whether the sampling time slot matches a corresponding sampling period, and executing a step of determining the sampling configuration corresponding to the sampling time slot in the sampling refresh period based on the preset sampling rule when the sampling time slot matches the corresponding sampling period.

6. The method according to claim 2, wherein one of the sampling time slots corresponds to a sampling period, and before the determining, based on a preset sampling rule, a sampling configuration corresponding to a sampling time slot in a sampling refresh period, the method comprises:

determining, based on a preset sampling refresh period, whether the sampling time slot matches a corresponding sampling period, and executing a step of determining the sampling configuration corresponding to the sampling time slot in the sampling refresh period based on the preset sampling rule when the sampling time slot matches the corresponding sampling period.

7. The method according to claim 1, wherein the sample data is PPG data or electrocardiogram data, the PPG data is data generated from a photoplethysmogram waveform generated from a photoplethysmography measurement method.

8. An apparatus for detecting biometric data, comprising a sampling and managing apparatus for biometric data and a plurality of sampling channels, the sampling and managing apparatus being configured for controlling, based on a sampling configuration of a plurality of sampling configurations corresponding to a sampling time slot in a sampling refresh period, a sampling channel of a plurality of sampling channels corresponding to the sampling time slot to sample a target signal reflecting the biometric data, the sampling refresh period comprising a plurality of sampling time slots, each of the sampling channels comprising an analog front-end and an analog-to-digital converter connected to the analog front-end, the sampling and managing apparatus comprising: a time slot configuration table, a sampling configuration table, a sampling refresh period controller, a sampling time slot controller, a controller of a LED driver, analog front-end controllers, and analog-to-digital converter controllers, wherein the time slot configuration table comprises a correspondence between slot identifiers for the plurality of sampling time slots and configuration identifiers for the plurality of sampling configurations, and the sampling configuration table comprises a correspondence between the configuration identifiers and the plurality of sampling configurations, each of the sampling configurations comprising a sampling channel enabling parameter and a sampling process control parameter, the sampling channel enabling parameter being used for switching on or off the sampling channel corresponding to the sampling configuration, and the sampling process control parameter being used for setting a sampling parameter used by the sampling channel corresponding to the sampling configuration during sampling, wherein the sampling refresh period controller is configured to control the sampling refresh period, and to control the sampling time slot controller to read the time slot configuration table and the sampling configuration table in units of the sampling refresh period, the sampling time slot controller is configured to, for each sampling time slot in the sampling refresh period, under the control of the sampling refresh period controller:

read the time slot configuration table based on a slot identifier for the sampling time slot to determine a configuration identifier for a sampling configuration corresponding to the slot identifier, read the sampling configuration table based on the configuration identifier to determine the sampling channel enabling parameter and the sampling process control parameter corresponding to the sampling time slot, and generate trigger pulses for the controller of the LED driver, the analog front-end controllers and the analog-to-digital converter controllers corresponding to the sampling time slot based on the sampling channel enabling parameter and the sampling process control parameter corresponding to the sampling time slot; and the controller of the LED driver is configured to sample the trigger pulses for the LED driver and generate a LED driver control sequence to control a LED driving unit to drive or stop driving a LED;

the analog front-end controllers are configured to sample the trigger pulses for the analog front-end controllers and generate analog front-end control sequences to control the analog front-ends to start or stop collecting a target signal from a respective photodiode, and the analog-to-digital converter controllers are configured to sample the trigger pulses for the analog-to-digital converter controller and generate analog-to-digital converter control sequences to control the analog-to-digital converters to start or stop converting the collected target signal from the respective photodiode to corresponding sample data.

* * * * *